Sept. 16, 1969 S. D. McGREDY Plant Pat. 2,919
ROSE PLANT
Filed March 17, 1967
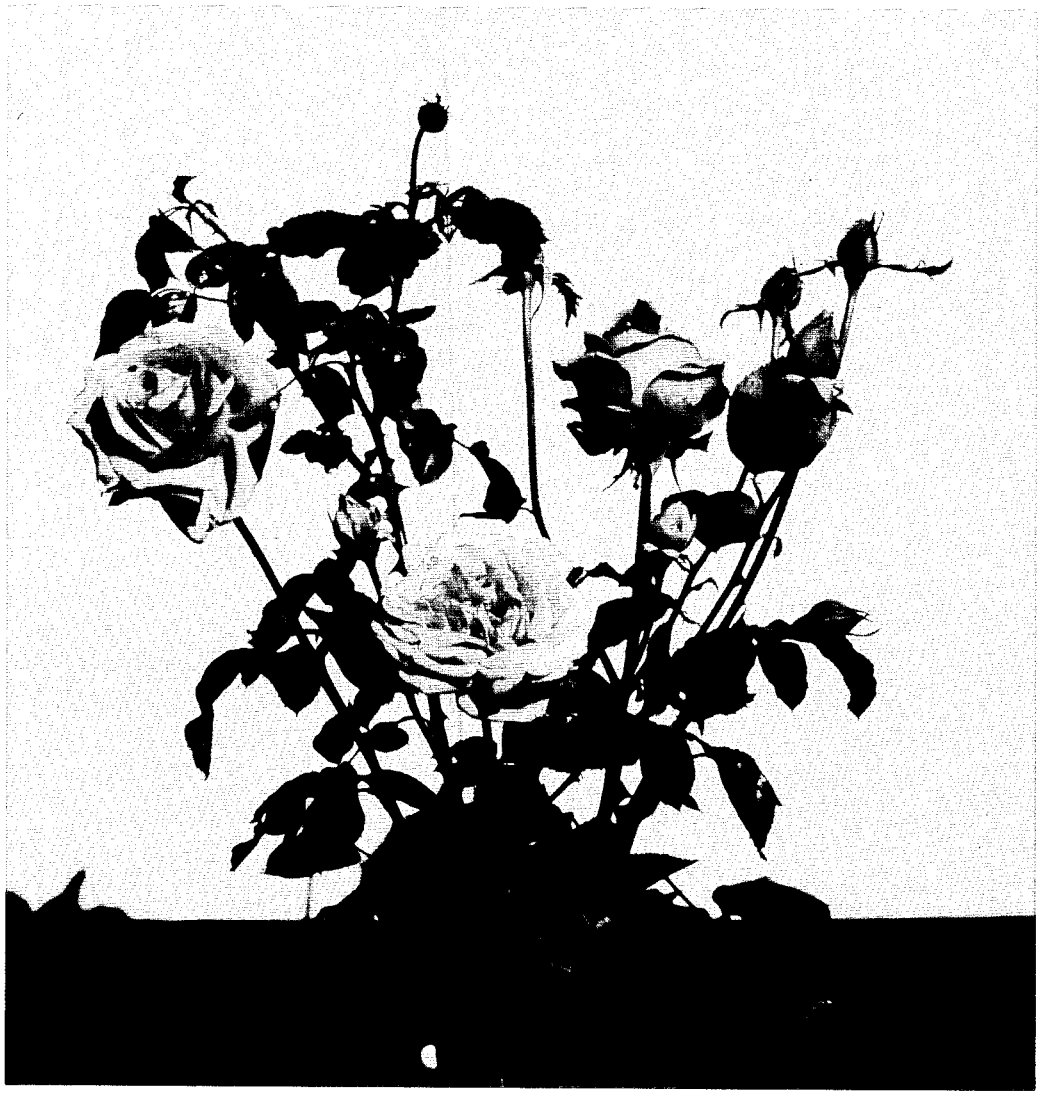

United States Patent Office

Plant Pat. 2,919
Patented Sept. 16, 1969

2,919
ROSE PLANT

Samuel Darragh McGredy, % Samuel McGredy & Son Limited, Royal Nurseries, Portadown, Northern Ireland Filed Mar. 17, 1967, Ser. No. 624,103
Int. Cl. A01h 5/02
U.S. Cl. Plt.—19 1 Claim The invention relates to a new and distinct variety of rose plant of the hybrid tea class originated by me in 1959 as a consequence of a breeding program begun in 1958. The parentage of my new rose plant is as follows:

Seed parent: Queen Elizabeth, P.P. No. 1,259.
Pollen parent: McGredy's Yellow.

The object of the cross was to combine the vigor, disease resistance, winter hardiness and large foliage of Queen Elizabeth (P.P. No. 1,259) with the floriferousness, lightly branched plant habit, large individual well formed flowers of McGredy's Yellow (non.pat.) and to enhance the color of Queen Elizabeth which is often dull, by introducing a yellow base color by way of McGredy's Yellow into the bloom of the progeny.

These objectives were achieved along with other desirable improvements as evidenced by the following unique combination of characteristics which are outstanding in the new variety and which distinguish it from its parents as well as from all other varieties of which I am aware.

My new variety is primarily characterized by: a large, well formed plant of vigor and stature intermediate between Queen Elizabeth and McGredy's Yellow, reaching heights from moderate pruning of 48"–60". The plant is more upright than McGredy's Yellow and more spreading and branched than Queen Elizabeth, but flowers tend to be produced at the top of the plant like Queen Elizabeth. The canes are stout green (Munsell 5GY 5/4) when young, dull grey green when mature, moderately armed. The thorns are large, slightly hooked reddish when young (Munsell 7.5YR) with lighter tips, tan to brown when old.

The foliage is large, 5–7 leaflets, abundant, dark green, semi-glossy. The leaflets are round, ovate, tending to be broader in relation to length than most common HT roses marketed today. Both apex and base are acute and the leaf margin is simple serrate. The color of the leaflets is dark green above (Munsell 715GY 4/6), somewhat lighter green and duller below (Munsell 7.5GY 5/4) when mature. The young foliage is light yellowish-green above (Munsell 10Y 4/6) tinged with red, especially on the margins (Munsell 5R), and lighter below. The flowering branches are stout and erect, holding the flower well, and the same color and armature as the canes. The peduncle is stout, stiff, of medium length, reddish-green and bearing moderate numbers of small reddish prickles. Asexual reproduction was by budding through a series of annual propagations at Portadown, N. Ireland.

The bud is ovoid, pointed, of medium size. The sepals are ornate with fimbriate, foliaceous appendages extending ¼th the length of the bud above the bud, and often longer. The calyx is the same color and pattern as the foliage.

The petals are of medium size, ovoid, rosy-pink (Munsell 10RP) with a yellow claw (Munsell N/Y). The reverse of the petals is slightly darker than the face (Munsell 5/14 vs. 5/12). The flower opens well under adverse weather conditions and lasts 4–5 days. The open bloom is 3½ to 4½ inches across, often larger in spring and fall. The bloom is fully double, with from 40–50 petals, nicely whorled, making the variety excellent for exhibition. The flower form is globular, becoming cupped, but high centered, and finally at maturity, high centered with the outer petals loosely rolled outward. The substance of the petals is good although the texture is soft and satiny. The petal shape is obovate and mucronate. The anthers are usually few and the ovaries often deformed. The fertility of the variety is low. Fragrance is very slight and musky.

Having thus disclosed my invention, I claim:

1. A new and distinct variety of rose plant of the hybrid tea class substantially as herein shown and described primarily characterized by: a viorous, upright growing plant, very free blooming, with highly disease resistant, broad, dark green, abundant foliage, and large very full blooms, borne individually, which are a warm shade of rosy pink, slightly darker on the reverse of the petals than above, with a perfectly imbricated and whorled petal arrangement, the combination of which gives a particular sculptured effect and depth to the bloom.

No references cited.

ROBERT E. BAGWILL, Primary Examiner